Figure 1:
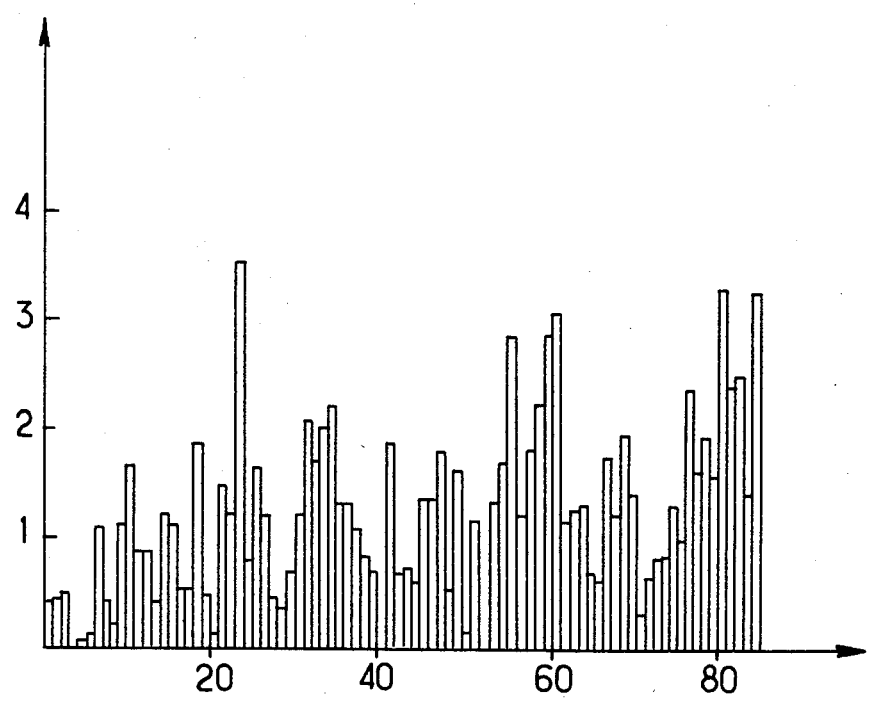

United States Patent [19]

Strosberg et al.

[11] Patent Number: 4,780,407
[45] Date of Patent: Oct. 25, 1988

[54] MONOCLONAL ANTIBODIES TO LEGIONELLA, A PROCESS FOR THEIR PREPARATION AND THEIR USE IN THE DETERMINATION OF LEGIONELLA PNEUMOPHILA

[75] Inventors: Arthur D. Strosberg; Jean G. Guillet; Johan Hoebeke; Cuong Tram, all of Paris, France

[73] Assignees: Institut Pasteur; Centre National de la Recherche Scientifique, both of Paris, France

[21] Appl. No.: 73,864

[22] Filed: Jul. 1, 1987

Related U.S. Application Data

[63] Continuation of Ser. No. 581,194, Feb. 17, 1984, abandoned.

[30] Foreign Application Priority Data

Feb. 21, 1983 [FR] France ................ 83 02789

[51] Int. Cl.$^4$ ............... G01N 33/569; G01N 33/577; C12N 5/00; A61K 39/40
[52] U.S. Cl. .................. 435/7; 435/240.27; 435/172.2; 435/810; 424/87; 424/88; 436/548; 530/387; 935/103; 935/107; 935/110
[58] Field of Search ............. 435/7, 34, 39, 172.2, 435/948, 240.27, 810; 436/548; 530/387; 424/88, 87; 935/103, 106, 110

[56] References Cited

U.S. PATENT DOCUMENTS 4,376,110  3/1983  David et al. ............... 436/513

OTHER PUBLICATIONS

Wong et al., Annals of Internal Medicine, 90: 634–638, 1979.
Köhler et al., Nature, vol. 256: 495–497, 1975.
Para et al., J. of Clinical Microbiology, 18: 895–900, 1983.
Biological Abstracts, vol. 73, 1982, No. 32777; C. R. Rinaldo, Jr. et al.: "Growth of the Pittsburgh Pneumonia Agent in Animal Cell Cultures", & Infect Immun 33(3): 939–943, 1981.

*Primary Examiner*—Esther M. Kepplinger
*Attorney, Agent, or Firm*—Burns, Doane, Swecker & Mathis

[57] ABSTRACT

A process to produce hybrid cell lines, which produce monoclonal antibodies to Legionella pneumophila. Cell lines are produced by fusion of immunized mouse splenocytes to these bacteria with non secreting myeloma cells.

Monoclonal antibodies are useful for diagnosis of diseases due to *Legionella pneumophilia*, for detection of these bacteria in environment, for the production of vaccines.

11 Claims, 4 Drawing Sheets

MONOCLONAL ANTIBODIES TO LEGIONELLA, A PROCESS FOR THEIR PREPARATION AND THEIR USE IN THE DETERMINATION OF LEGIONELLA PNEUMOPHILA

This application is a continuation of application Ser. No. 581,194, filed Feb. 17, 1984, now abandoned.

The present invention relates to monoclonal antibodies to Legionella; it also relates to a process for the preparation of these antibodies, hybrid murine cell lines which produce such antibodies, and to the biological applications thereof, in particular in the prevention and diagnosis of pneumonias and the detection and identification of Legionella bacteria in the environment.

The introduction of serological diagnostic tests to study the etiology of atypical pneumonia has shown that the principal pathogenic agent of this disease was the bacteria *Legionella pneumophila* (Macfarlane, J. T. et al. 1982. Hospital Study of adult community acquired pneumonia. Lancet 1982; 255–258). This disease has been found sporadically or in the form of an epidemic, in particular, in the hospital field. It has thus proved of interest to develop a standardized method of diagnostic, which is useful not only to detect human antibodies to Legionella, which appear belatedly during an infection, but also to detect minor amounts of the bacteria themselves or of bacterial antigens, collected in the expectorations, the bronchotracheal lavages samples and the urinees, This type of diagnosis is only reliable if antibodies against the specific antigens of Legionella which do not display cross-reactions with other bacteria, are available.

According to the present invention, Hybrid cell lines which produce monoclonal antibodies to Legionella which can be used for the diagnosis of pneumonias are provided. These monoclonal antibodies have a high, stable and constant affinity to Legionella antigens, and they can be used for direct quantitative determination of the infectious agent in the first stages of the disease and for determination of antibodies to Legionella in the blood of the patient in the course of later phases of the disease.

The present invention thus relates to hybrid murine cell lines which produce monoclonal antibodies to Legionella having a high titre and a high specificity.

The hybrid murine cell lines according to the invention are produced by fusion between myeloma cells from mice and splenocytes from mice immunized against Legionella, such as the species *Legionella pneumophila*.

The fusion of myeloma cells derived from mice with Lymphocytes cells from immunized mice was proposed for the first time in 1975 by KOHLER and MILSTEIN [Nature 256 495–497 (1975)]. The fusion method, also called "hybrid cells method" has since been chiefly utilized for the production of monoclonal antibodies. However, until the present time, to the knowledge of the Applicant, no antibodies to Legionella have ever been produced.

In its general aspect, the process according to the invention for the preparation of hybrid murine cell to Legionela lines comprises the following steps:

(1) immunization of mice with a given amount of dead Legionella bacteria;

(2) withdrawal of the spleen of the immunized mice after sacrifice and preparation of the splenocytes suspension;

(3) fusion between the spleen cells thus obtained and myeloma cells from mice in the presence of a fusion promoter;

(4) culture of the hybrid myeloma cells obtained in a selective medium on which non-fused myeloma cells, do not replicate, in the presence of appropriate nutritional elements; and (5) selection of the hybrid cells which produce the desired antibody and cloning of these cells.

The process according to the invention is applied to bacteria of the Legionellaceae family, of which at present a single genus is known, the genus Legionella, which includes several species, in particular *Legionella pneumophila*.

The first stage of the process according to the invention comprises immunization of mice by Legionella bacteria which have been killed by any means, for example by a chemical agent, such as formol, or by heat. The bacteria of a given sero-group, for example *Legionella pneumophila* sero-group I, are used. For more details on such bacteria, the following publication may be referred to: McDade, J. F. et al 1977, Legionnaire's disease: isolation of a bacterium and demonstration of its role in other respiratory diseases—N. Engl. J. Med. 297 1197–1203, mentioned by reference in the present description.

Particular examples which may be mentioned of bacteria which are suitable for the process according to the invention are: *Legionella pneumoniae* of sero-group I, strain Legionella pneumophila, Philadelphia strain 1, deposited at the "Center for Disease Control" Atlanta, Ga. USA under ATCC No. 331.52, on 15th Aug. 1979.

The process according to the invention will now be described with reference to *Legionella pneumophila* without thereby limiting the scope of the invention to this sole species of Legionella.

The immunization of mice is carried out in such a manner as to stimulate the memory of the cells for synthesis of antibodies, avoiding the formation of IgM, which have proved to be more unstable than IgG. The immunization protocol used according to the invention is that which provokes a secondary response.

The immunization method which is preferred for the purpose of the invention consists in injecting a given amount of the bacteria, which have been killed by heat, intravenously once a week for three consecutive weeks and then after a period of rest of three months, and three days before sampling of spleen cells and fusion, in injecting a boost of the same amount of dead bacteria intravenously.

The amount of bacteria used can be $10^6$ to $10^9$. 200 million bacteria which have been killed by heat are advantageously used.

After sacrifice of the animals, a suspension of spleen cells from mice is prepared. For this purpose, serum-free RPMI ® medium is injected into the spleen and the cells are washed three times in serum-free RPMI before being fused.

The murine myeloma cells used in the process according to the invention are non secreting NS-1 myeloma cells. For example, the strain of NS-1 myeloma cells provided by Dr. Goodfellow (Imperial Cancer Research Foundation, London) has been used. These cells have been selected for their sensitivity to aminopterin and grown in an appropriate medium containing nutritional substances. Such a medium can comprise, for example, an RPMI 1640 medium [such a medium is defined, for example, by MOORE et al. Culture of Normal Human Leucocytes J.A.M.A. 199 519-524, 196] containing 10% of fetal calf serum, 2 mM of glutamine, 1 mM of sodium pyruvate, 100 international units/ml of penicillin and 100 μg/ml of streptomycin; this medium will be called complete RPMI medium below. The myeloma cells used in the process according to the invention are non-secreting cells. Although secreting cells could also be used, it is preferable to use non-secreting cells in order to obtain homogenous antibodies.

The fusion of the cells, which constitutes the third stage of the process according to the invention, results from mixing the splenocytes from mice which have been immunized against *Legionella pneumophila* of a given sero-group, with non-secreting NS-1 myeloma cells derived from mice, in accordance with the method described by KOHLER and MILSTEIN [Nature 256 495-497 (1975)], in the presence of a fusion promoter, such as, for example, a polyethylene glycol. Advantageously, one NS-1 myeloma cell is used per 10 spleen cells and a polyethylene glycol having a molecular weight of 1,000 is used in an amount of 41% by weight, based on the medium.

After incubation at 37° C. in an atmosphere containing 10% of $CO_2$, the cells are washed with RPMI medium and suspended in complete RPMI medium, and the resulting hybrid cells are cultured in a selective medium suitable solely for the growing of the hybrid cells. Such a selective medium can consist of complete RPMI medium, to which 0.1 mM of hypoxanthine, 0.4 μM of aminopterin and 16 μM of thymidine have been added. It is known that myeloma cells which are devoid of the enzyme hypoxanthine-guanine-phosphoribosyl-transferase do not replicate in media containing hypoxanthine, aminopterin and thymidine. As a result, the myeloma cells which have not fused cannot replicate on the selective medium used.

The supernatant of the cultures are then assayed (in general 15 days after the fusion) in order to determine the presence of antibodies to *Legionella pneumophila* by an immuno-enzymatic test, and sub-cloning is carried out in the presence of nutritional cells (for example splenocytes). The sub-cloning is advantageously carried out by the method of limiting dilutions according to Oi, V.T. and L.A. Herzenberg 1980. Immunoglobulin-producing hybrid cell lines in "Selected Methods in Cellular Immunology" (Eds. Mishell, R. B. and Shrigi, S. M.) p.351, Fillman, San Francisco.

The above sub-cloning is advantageously carried out on micro-plates; the well of the said micro-plates containing a sole clone are selected and their supernatant are tested, for example, by the ELISA method so that only clones which produce the desired antibodies to Legionella with specificity for the bacterium used for the immunization of the mice and which have a high affinity and are stable, are isolated.

To obtain significant amounts of the monoclonal antibodies to *Legionella pneumophila*, the hybrid cells obtained which produce the said antibodies are injected into mice, which have been primed peritoneally with tetramethyl-pentadecane. After at least 15 days, the ascites, which contain significant amounts of the desired antibodies, are harvested.

The antibodies thus obtained are preserved by freezing at −20° C. No reduction in their titer has been observed after frequent thawing and freezing.

The monoclonal antibodies to Legionella obtained according to the invention are useful agents for detection of Legionella and diagnosis of legionelloses. They can be used either to detect the presence of small amounts of *Legionella pneumophila* bacteria in the first stages of the disease, or to determine the amount of antibodies to Legionella in the blood of patients in the later stages of the disease, or to detect the bacterial antigens in the urine.

The monoclonal antibodies according to the invention also have applications in therapeutics. They can be used to prepare vaccines. For example, known antigens can be isolated and purified by affinity chromatography with the use of a monoclonal antibody according to the invention. The antigens thus obtained can be used to prepare vaccines by conventional methods well-known to those skilled in the art. The disease can then be prevented by systematic vaccination of persons working in areas known as being "high risk areas" (hospital environment, hotels and the like).

The monoclonal antibodies according to the invention can also be used as therapeutic agent in cases of bacteremia. For this purpose, the antibodies, which have purified by affinity chromatography, are sterilized by filtration (0.2 μm Acrodisc) and injectable solutions containing monovalent Fab fragments of these antibodies are prepared in accordance with the method of PORTER R.R. Biochemical Journal 1959, 73, p.119-126. These solutions can be administered intravenously to patients by perfusion.

The monoclonal antibodies to Legionella according to the invention are particularly useful for systematic investigation of the bacteria in the ambient environment (for example in the water and air of a hospital), as much from the quantitative point of view as from the qualitative point of view. They thus enable, in particular, new natural strains to be isolated and to be precisely typified. They can especially be used to detect the presence of Legionella bacteria retained on filters fixed over the water and air intakes in a suspect ambient environment.

The monoclonal antibodies according to the invention can also be limited to an immunosorbent, and the combination can be used as a filter for isolating and concentrating the bacteria. The invention thus also related to immuno-sorbents to which the monoclonal antibodies according to the invention are bound; these immuno-sorbents are suitable for epidemiological detection. The immuno-sorbents used are conventional, such as Sephadex beads, on which the said monoclonal antibodies are immobilized. The immuno-sorbents can advantageously be in the form of immuno-sorbent pellets.

The antibodies according to the invention are particularly suitable for the above detections, especially by the immunofluorescente (direct or indirect) or immunoenzymatic (for example the ELISA method) assays. They can also be used in other determination methods, such as in radioimmunological methods. The invention thus also relates to immunological diagnostic kits, especially those using an immunoenzymatic or immunofluorescent method, which comprise a monoclonal antibody according to the invention as the principal immunological reactant.

Such kits chiefly contain the reactants at present used in these types of diagnostics, that is to say:

(1) for tests by immunofluorescence: monoclonal antibodies limited to a fluorochrome, buffers and appropriate supports; and (2) for tests by an enzymatic method: the monoclonal antibody, the enzyme, the substrates of enzyme to measure the enzymatic activity, the buffers and appropriate supports.

The invention thus also relates to the use of the said antibodies in the diagnosis of pneumonias, and kits for diagnosis by immunoenzymatic or immunofluorescence methods which comprise an antibody according to the invention as immunological reactant.

The monoclonal antibodies according to the invention are specific of the bacterium used for the immunization of the animals.

The preferred monoclonal antibodies according to the invention are monoclonal antibodies to *Legionella pneumophila* of sero-group I obtained from hybrid murine cell lines (*Legionella pneumophila* Philadelphia strain I), which originate from fusion according to the above process between splenocytes from mice immunized against *Legionella pneumophila* sero-group I and non-secreting NS-1 myeloma cells derived from mice.

Two distinct fusions have been carried out according to the invention and 28 lines of hybrid murine cells have been obtained, amongst which three lines, II-6, III-1 and III-7, have been selected and have been subcloned. The three following sub-clones II-6-18; III-1-12 and III-7-1 have then been selected. The lines of hybrid murine cells resulting from sub-cloning II-6-18 and III-1-12 were deposited in the Collection Nationale de Culture de Microorganismes (National Collection of Microorganism Cultures) of the Pasteur Institute in Paris (France), on 14th Feb. 1983, under Nos.:

I-220 for the line II-6-18,

I-219 for the line III-1-12.

The antibodies produced by these lines of cells have the following characteristics: The monoclonal antibodies produced by the cell line II-6-18 are $\gamma$-3 isotypes and their isoelectric point is 8.7; the monoclonal antibodies produced by the cell line II-1-12 are $\gamma$-2b isotypes and their isoelectric point is 6.5. The monoclonal antibodies produced by the cell ine III-7-1 are $\gamma$-1 isotypes.

EXAMPLE 1

Production of Monoclonal Antibodies to *Legionella pneumophila* of sero-group I

*Legionella pneumophila* bacteria of sero-group I (*Legionella pneumophila* Philadelphia strain 1) were used for the immunization of the mice in this example, since 80% or more of legionelloses are caused by bacteria from sero-group I (cases known in France).

The *Legionella pneumophila* bacteria of sero-group I (reference strain Philadelphia 1) had been grown in a medium consisting essentially of agar completed with corpuscular extracts, yeast extracts, defibrinated horse blood, cystine and ferric ions. The medium was buffered at pH 6.9 by addition of potassium hydroxide and other precursors which stimulate growth.

After incubation at 37° C. under anaerobic conditions for 2 or 3 days, the *Legionella pneumophila* were harvested in a tube containing a physiological solution buffered at pH 7.4 with phosphate. The suspension obtained was homogenized by vortex motion and the bacteria were killed by boiling for 20 minutes. The suspension of dead bacteria was tested for 7 days to detect the possible presence of live bacteria. The suspension of dead bacteria was adjusted to $2\times10^9$ bacteria/ml by measuring the turbidity with a MaoFarl and No. 4. tube.

I-Immunization

Balb/c mice were immunized in accordance with the method described above, that is to say Balb/c mice were injected intravenously once a week with 200 million bacteria which had been killed by heat, for three consecutive weeks. After a rest period of three months, the mice were given an intravenous boost of the same amount of bacteria (200 million) three days before the splenocytes were used for the fusion.

2-Fusion

NS-1 Murine myeloma cells provided by Doctor Goodfellow (Imperial Cancer Research Foundation, London) were used. They were selected for their sensitivity to aminopterin and cultured on RPMI medium containing 10% of fetal calf serum, 2 mM of glutamine, 1 mM of sodium pyruvate, 100 international units/ml of penicillin and 100 $\mu$g/ml of streptomycin.

The splenocytes were dispersed by introduction of serum-free RPMI medium into the spleen of the hyperimmunized mice and were washed three times in RPMI medium before fusion.

The NS-1 myeloma cells and the spleen cells from two spleens were then fused in a ratio of one myeloma cell to 10 splenocytes in the presence of 41% of polyethylene glycol of molecular weight 1,000 (Merck), in accordance with the method of KOHLER and MILSTEIN [Nature 256 495–497 (1975)], and were then washed with RPMI medium and suspended in 100 ml of complete RPMI medium. The cells were then redistributed in Nunclon micro-plates (24 wells per plate) in an amount of 1 ml/well, containing 0.22 million cells. After 24 hours, 1 ml/well of selective medium consisting of complete RPMI medium containing 0.1 mM of hypoxanthine, 0.4 $\mu$M of aminopterin and 16 $\mu$M of thymidine was added. Aliquot portions of the selective medium were replaced on the 3rd, 6th and 10th days after fusion. After 15 days, the hybridomes which remained were cultured on complete RPMI medium, supplemented with hypoxanthine and thymidine, and 28 days after the fusion, the presence of antibodies to Legionella in the supernatant fluid of the cultures was investigated for the first time. The clones were then cultured progressively on normal complete RPMI medium.

Six positive cultures were sub-cloned by the limiting dilution method according to Oi, V.T. and L.A. Herzenberg 1980 Immunoglobulin-producing hybrid cell lines in "Selected Methods in Cellular Immunology" (Eds. Mishell, R.B. and Shrigi, S.M. p. 351, Fillman, San Francisco). The cells were redistributed in the wells of a Nunclon microplate in an amount of 0.05 ml/well, with 0.3 million spleen cells as nutritive cells. After 10 days, the wells containing a sole clone were selected and, 5 days later, the supernatants were tested to determine the presence of antibodies to *Legionella pneumophila.*

Three sub-clones originating from three different clones were selected and injected into Balb/c mice in order to obtain large amounts of antibody. For this purpose, mature female Balb/c mice were "primed" intraperitoneally with 0.3 ml of tetramethyl-pentadecane. After 4 days, 20 million hybrid cells were injected into mice. After at least 15 days, the ascites were harvested and their anti-Legionella activity was tested. In accordance with the above procedure, two different fusions were effected and the sub-clones II-6-18 and III-1-12 were selected and have been deposited in the Collection Nationale de Culture de Microorganismes (National Collection of Microorganism Cultures) under numbers I-219 and I-220 as indicated above.

EXAMPLE 2

Characterization of the Resulting Antibodies by the ELISA Method

The antibodies obtained according to Example 1 were tested to determine their anti-Legionella activity by the immunoenzymatic method, which is well-known under the name of the ELISA method.

The micro wells in a NUNC-ELISA plate were filled with 0.05 ml of a 10 µg/ml solution of polylysine (marketed by Messrs. Sigma). After one hour at the ambient temperature, the wells were emptied and 0.05 ml of a suspension of bacteria which had been killed by heat or by formol was distributed in each well and evaporated at 50° C. To avoid non-specific adsorption of the antibodies, the wells were also treated at room temperature with 3% strength of bovine serum albumin in a saline solution buffered with phosphate (PBS) for one hour. The wells were then washed once with PBS containing 0.1% of bovine serum albumin.

The supernatant fluids of the hybrid cell cultures or the ascitic fluids to be tested were diluted in PBS containing 0.1% of bovine serum albumin; 0.05 ml of these dilutions were incubated in the wells for one hour at 37° C. After washing three times in PBS containing 0.1% of bovine serum albumin (BSA), 0.05 ml of sheep immunoglobulins to mouse immunoglobulins limited to horseradish peroxidase (supplied by Institut Pasteur Production, Paris) to a dilution of 1:500 were added. Two control series were prepared by incubating the above con]ugate in wells:

(1) which had not previously been incubated with the antibodies to Legionella from mice, or (2) which had been incubated with immunoglobulins from mice or with ascitic fluids which were non-specific in respect of Legionella.

After one hour of incubation with the conjugate, the wells were washed three times with PBS and enzyme substrate (2.5 mM of $H_2O_2$ and 2 mM of 2,2'-azi-nodi-3-ethyl-benzothiazoline-sulfonate (ABTS) in an acetate/phosphate buffer, pH=6.5) is then added. After 30 minutes, the optical density of each well was with an optical photometer from ARTEK Company and the plates were photographed.

Out of the 85 wells containing hybrid cells, 28 positive wells were detected by this method, using the strict characteristic of three times the controls to conclude to positiveness. The results obtained are shown in FIG. 1, in which the optical density (O. D.) at 405 nm, is plotted as the ordinates and the wells are plotted as the abscissas.

Of the 28 positive wells, 10 were tested to verify the sero specificity of the monoclonal antibodies according to the invention in respect of sero-group I.

For this purpose, the same test as that above was carried out with wells incubated with a suspension of bacteria of different sero types, and it was found that the supernatant of the hybrid cell cultures were clearly positive in respect of sero-group I, reacted only to the extent of one third or one-half with a mixture of sero-groups I, II and III, but did not react with a mixture of sero-groups IV, V and VI or with the atypical strains N, T or W.

Figure 2:
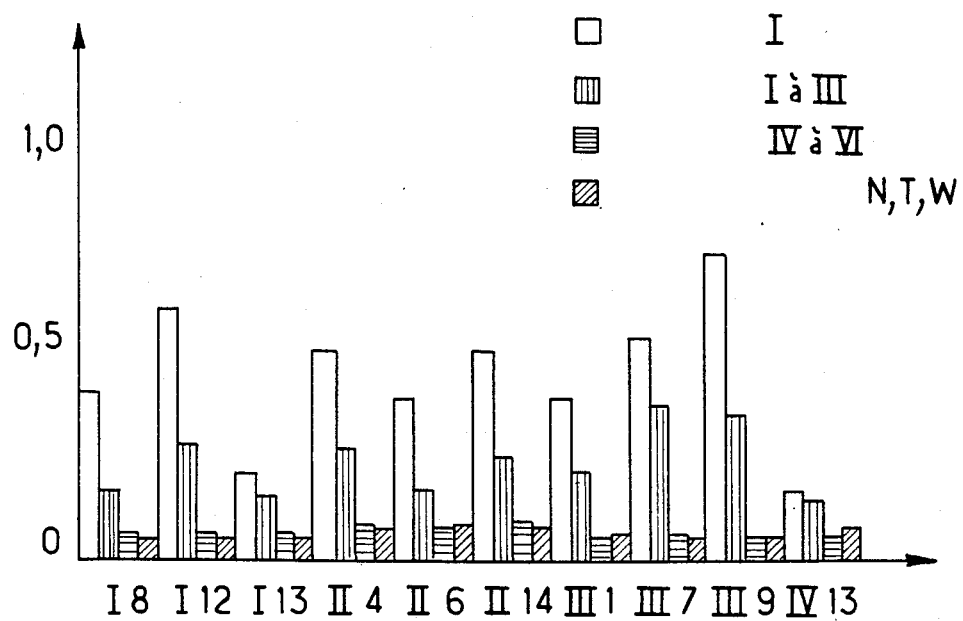

The results obtained are shown on FIG. 2, in which the optical density at 405 nm has been plotted as the ordinates and the reference of the clones tested has been plotted as the abscissas.

EXAMPLE 3

Serological Characterization of Two Monoclonal Antibodies Obtained From Ascitic Fluids Sub-cloning of six cultures of hybrid cells was effected in order to obtain homogenous antibodies. In these cultures, those which gave stable hybrids after sub-cloning were selected. Two of these sub-clones (II-6-18 and III-1-12) were injected into mice in accordance with the procedure described above, and the ascitic fluids obtained were used.

The isotypes of two monoclonal antibodies thus obtained were tested by the indirect ELISA method using mono-specific polyclonal antibodies from rabbits against various isotypes of murine immunoglobulins.

The ascitic fluids obtained after injection of the sub-clone II-6-18 gave antibodies to Legionella of the γ-3 isotype, and with the sub-clone III-1-12, antibodies of the γ-2b isotypes were obtained.

The two antibodies thus obtained were then tested against nine different strains of Legionella by the ELISA method and by indirect immunofluorescence. Only the strain of sero-group I was recognized by these two tests.

The ELISA method was also used to verify the possible existence of cross-reactions with other bacteria, using *Klebsiella pneumoniae* and *Mycoplasma pneumoniae* as antigens in the ELISA test. No cross-reaction was observed with the above two antibodies.

EXAMPLE 4

Determination of the Titre of the Ascitic Fluids Obtained With the Clone II-6-18 for the Purpose of Diagnosis The minimum amount of bacteria which give a positive result by the ELISA method was investigated.

Figure 3A:
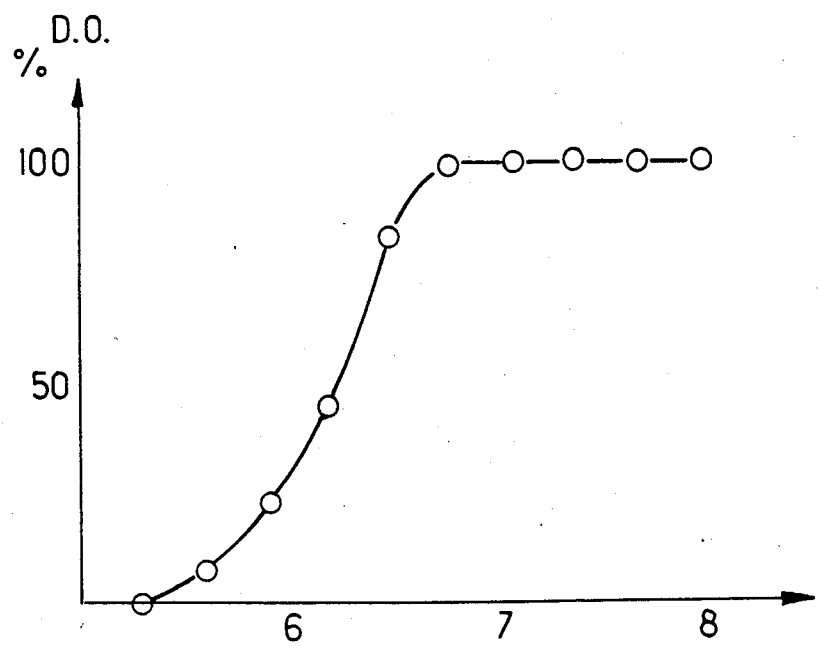
Figure 3B:
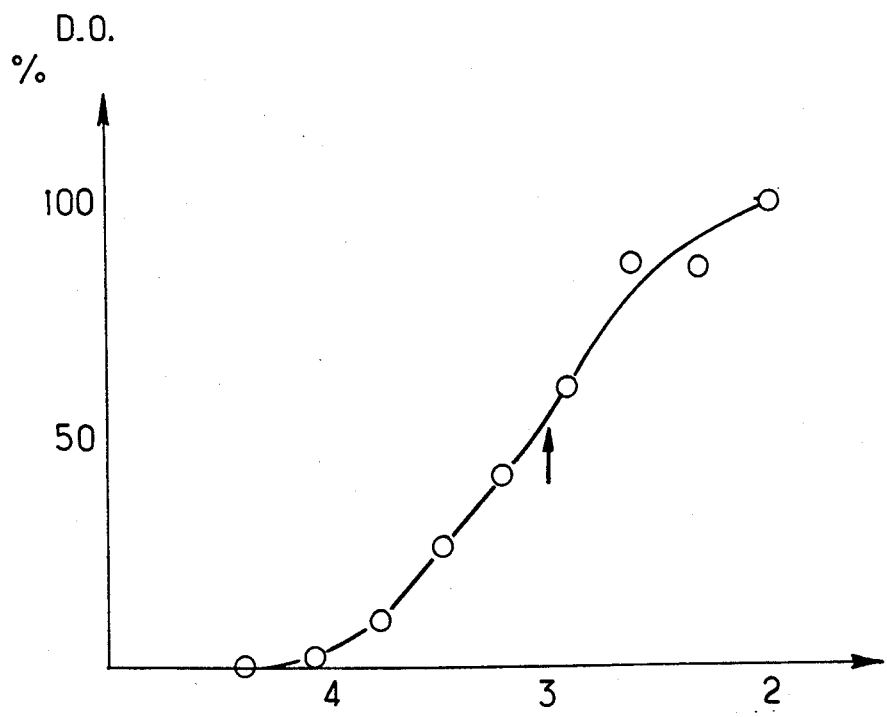

The results obtained are shown in FIGS. 3a and 3b.

In FIG. 3a, the optical density in percent, based on the maximum value obtained in the preceding test (% maximum) is plotted as the ordinates and the logarithm of the amount of bacteria is plotted as the abscissas.

From this figure, it can be seen that the amounts of bacteria giving 50% of the maximum response was 2 million. It can be seen that small amounts of 0.5 million can also be detected with significant precision.

The titre of ascitic fluid for 2 million bacteria is shown in FIG. 3b, in which the logarithm of the dilution of the ascitic fluid has been plotted as the abscissas and the optical density (% maximum) has been plotted as the ordinates. It can be seen that 50% of the maximum response is obtained with a dilution of 1/1000.

The monoclonal antibodies can be used in two ways: either in a competition test with Legionella bacteria themselves, for quantification of these; or in a competition test with antiserum containing antibodies to Legionella, to determine their titres.

Figure 4A:
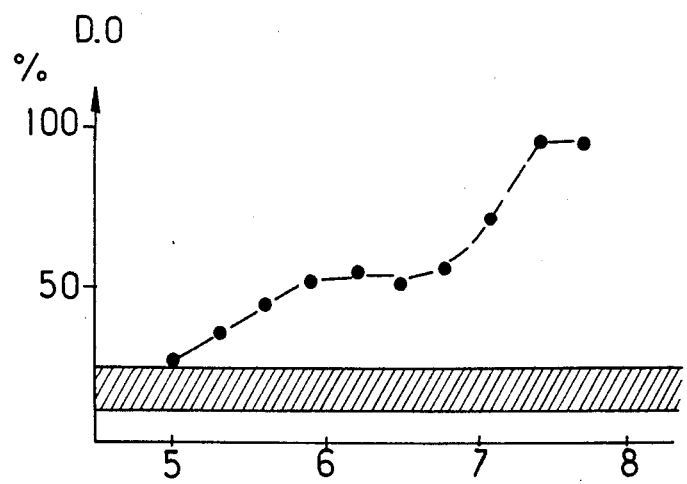
Figure 4B:
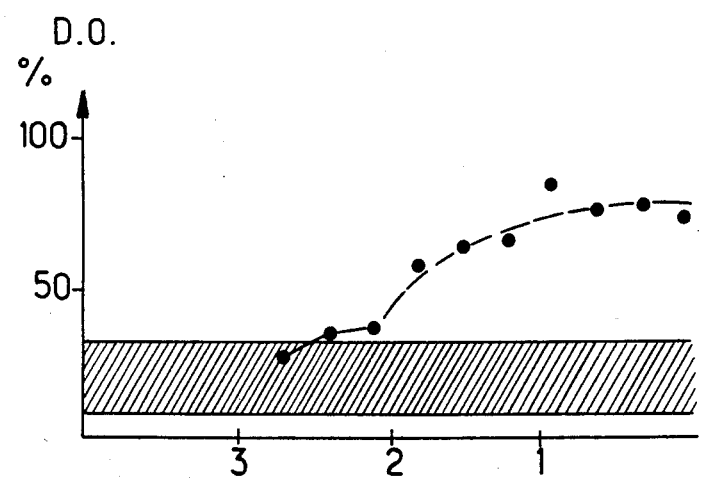

The monoclonal antibodies have been used in these two types of assays; the results obtained are shown in FIGS. 4a and 4b.

FIG. 4a relates to a competition test with the bacteria *Legionella pneumophila;* the ascitic fluid was used at a dilution of 1/1000 in wells containing 2 million bacteria in the presence of various amounts of bacteria (the logarithm of the amount of bacteria is plotted as the abscissas and the optical density in % inhibition is plotted as the ordinates). As can be seen from this figure, an inhibition of 50% was obtained with 1 to 10 million bacteria. Since such amounts are easily present in the expectorations and the bronchotracheal lavages of patients, the ELISA competition test can be used to diagnose legionelloses in the initial stage of the disease.

The hatched area shows the mean and standard deviation from the control values obtained by competition with *Klebsiella pneumoniae.*

FIG. 4b relates to a competition test with various dilutions of the antiserum to Legionella from rabbits in wells containing 2 million bacteria. On this figure, the optical density in % inhibition has been plotted as the ordinates and the logarithm of the titre of the serum has been plotted as the abscissas. The hatched area corresponds to the mean and standard deviation obtained by competition with the serum from preimmunized rabbits. These results show that the titre of an antiserum can be determined by inhibition.

EXAMPLE 5

Simple and Rapid Process for the Detection of Legionella Bacteria in the Environment 1. WATER: the water to be tested was sampled directly from the water outlets in accordance with the procedure below:

Millipore ® filters (0.45 μm Acrodisc from GELMAN) were attached to the water inlets with a 5 ml syringe;

(a) After saturation at 37° C. in PBS with 3% of BSA for half an hour, the various filters were contacted with a solution of monoclonal antibodies according to the invention, diluted to a final dilution of 1/50, at 37° C. for 1 hour.

Three washings (3×10 ml) were then carried out with a 5 ml syringes at the ambient temperature, using a solution of PBS with 0.1% of BSA.

(b) The filters were then exposed to a solution of antibodies(to Ig of mice) limited to peroxidase (Pasteur Production), diluted to a final dilution of 1/500, at a temperature of 37° C. for 1 hour.

(c) Finally, the filters were washed (3×10 ml) with PBS buffer, before being contacted with the enzyme substrate($H_2O_2$-ABTS, marketed by Sigma), and the results were read after 30 minutes.

The controls were liquids (Biocedra sterile water) devoid of any contamination.

By the above procedure, it is possible to detect the presence of Legionella in the water of a hospital establishment in a very short time, about 200 minutes, whereas up until the present time, such a detecton required culture of the bacteria.

2 AIR: the air to be tested was sampled directly at the air outlets of various air-conditioning systems:

The same Millipore ® filters as those above were used, together with a simple system (funnel attached hermetically on the ventilation grill) for collecting the bacteria on the filters, that is to say the bacteria from in the air extracted.

It will be noted that in the two above cases, the bacteria can be killed on the filters using, for example, a formol solution, which can easily be removed after its bactericidal action.

EXAMPLE 6

Determination of the Antigen in the Urine of Patients

The monoclonal antibodies obtained according to Example 1 were used in a competition test of the ELISA type. The purified antibodies were put onto the surface of wells of a plastic plate, filling wells with 50 μl of a solution containing 10 μg/ml of antibodies. The urine was then introduced into the wells; after leaving to stand at 4° C. overnight, the wells were washed and the antibody, limited to an enzyme, was introduced to carry out the ELISA method. The equivalent of antigen to 1000 bacteria per sample is detected by the method thus described.

We claim:

1. A murine hybrid cell line producing antibodies to *Legionella pneumophila* of sero-group I selected from the group consisting of CNCM I-219 and CNCM I-220.

2. A monoclonal antibody to Legionella produced by a hybrid cell line as claimed in claim 1.

3. A process for the qualitative and quantitative immunological determination of *Legionella pneumophila* bacteria in biological fluids or int he environment, said process comprising attaching filters capable of retaining bacteria to air or water inlets; removing said filters from said air or water inlets; contacting the filters with a solution of monoclonal antibody as claimed in claim 2; washing said filter; and determining the *Legionella pneumophila* bacteria content by an immunoenzymatic method of immunofluorescence.

4. The process for the qualitative and quantitative immunological determination of *Legionella pneumophila* bacteria as claimed in claim 3, wherein said antibody is produced by the murine hybrid cell line deposited in the Collection Nationale de Cultures de Microorganismes (National Collection of Microorganism Cultures) of the Institut Pasteur - Paris (France) under No. I-220, which antibody is of the γ-3 isotype.

5. The process for the qualitative and quantitative immunological determination of *Legionella pneumophila* bacteria as claimed in claim 3, wherein said antibody is produced by the murine hybrid cell line depostited in the Collection Nationale de Cultures de Microorganismes (National Collection of Microorganism Cultures) of the Institut Pasteur - Paris (France) under No. I-219, which antibody is of the γ-2b isotype.

6. A monoclonal antibody, produced by the murine hybrid cell line deposited in the Collection Nationale de Cultures de Microorganismes (National Collection of Microorganism Cultures) of the Institut Pasteur - Paris (France) under No. I-220, which antibody is of the γ-3 isotype.

7. A monoclonal antibody produced by the murine hybrid cell line deposited in the Collection Nationale de Cultures de Microorganismes (National Collection of Microorganism Cultures) of the Institut Pasteur-Paris (France) under No. I-219, which antibody is of the γ-2b isotype.

8. A diagnostic kit useful in the detection of *Legionella pneumophila* bacteria which is present in a biological sample using an immunoenzymatic method or immunfluorescence, which contains as the immunological reactant, a monoclonal antibody in an amount suitable for detecting the presence of *Legionella pneumo-*

*phila* bacteria, said monoclonal antibody to Legionella produced by a hybrid cell line obtained by a process which comprises fusing splenocytes from mice which have been immunized with bacteria of the family Legionella with non-secreting myeloma cells derived from mice, wherein said antibody is produced by the murine hybrid cell line deposited in the Collection Nationale de Cultures de Microorganismes (National Collection of Microorganism Cultures) of the Institut Pasteur-Paris (France) under No. I-220, which antibody is of the γ-3 isotype and diagnostically acceptable components for said detection.

9. A diagnostic kit useful in the detection of *Legionella pneumophila* bacteria which is present in a biological sample using an immunoenzymatic method or immunofluorescence, which contains as the immunological reactant, a monoclonal antibody in an amount suitable for detecting the presence of *Legionella pneumophila* bacteria, said monoclonal antibody to Legionella produced by a hybrid cell line obtained by a process which comprises fusing splenocytes from mice which have been non-secreting myeloma cells derived from mice, wherein said antibody is produced by the murine hybrid cell line deposited in the Collection Nationale de Cultures de Microorganismes (National Collection of Microorganism Cultures) of the Institut Pasteur Paris-(France) under No. I-219, which antibody is of the γ-2b isotype and diagnostically acceptable components for said detection.

10. A vaccine composition useful in combatting the effects of disease caused by Legionella bacteria comprising a monoclonal antibody to Legionella produced by a hybrid cell line obtained by a process which comprises fusing splenocytes from mice which have been immunized with bacteria of the family Legionella with non-secreting myeloma cells derived from mice, wherein said antibody is produced by the murine hybrid cell line deposited in the Collection Nationale de Cultures de Microorganismes (National Collection of Microorganism Cultures) of the Institut Pasteur - Paris (France) under No. I-220, which antibody is of the γ-3 isotype and a pharmaceutically acceptable carrier therefor.

11. A vaccine composition useful in combatting the effects of disease caused by Legionella bacteria comprising a monoclonal antibody to Legionella produced by a hybrid cell line obtained by a process which comprises fusing splenocytes from mice which have been immunized with bacteria of the family Legionella with non-secreting myeloma cells derived from mice, wherein said antibody is produced by the murine hybrid cell line deposited in the Collection Nationale de Cultures de Microorganismes (National Collection of Microorganism Cultures) of the Institut Pasteur-Paris (France) under No. I-219, which antibody is of the γ-2b isotype and a pharmaceutically acceptable carrier therefor.

* * * * *